US008961384B2

(12) United States Patent
Schmidt

(10) Patent No.: US 8,961,384 B2
(45) Date of Patent: Feb. 24, 2015

(54) HEALTH APPLICATIONS OF A DOUBLE HELIX CONDUCTOR

(71) Applicant: Lifewave, Inc., San Diego, CA (US)

(72) Inventor: David G. Schmidt, Poway, CA (US)

(73) Assignee: Medical Energetics Ltd, Galway (IE)

( * ) Notice: Subject to any disclaimer, the term of this patent is extended or adjusted under 35 U.S.C. 154(b) by 2 days.

(21) Appl. No.: 14/103,658

(22) Filed: Dec. 11, 2013

(65) Prior Publication Data

US 2014/0100412 A1 Apr. 10, 2014

Related U.S. Application Data

(63) Continuation of application No. 13/458,716, filed on Apr. 27, 2012, now Pat. No. 8,652,023.

(60) Provisional application No. 61/633,593, filed on Feb. 13, 2012.

(51) Int. Cl.
*A61N 1/00* (2006.01)
*A61N 2/02* (2006.01)
*A61N 2/00* (2006.01)

(52) U.S. Cl.
CPC .. *A61N 2/02* (2013.01); *A61N 2/008* (2013.01)
USPC ............. 600/13; 128/897; 128/898; 128/899; 47/1.3; 336/229; 336/65; 336/68; 336/73; 336/185; 336/199; 336/206; 336/208

(58) Field of Classification Search
USPC .............. 600/9–14; 336/229, 65, 68, 73, 185; 336/199, 206, 208; 47/1, 3; 128/897–899
See application file for complete search history.

(56) References Cited

U.S. PATENT DOCUMENTS

| 2,035,274 | A | * | 3/1936 | Mougey | 174/29 |
| 3,066,295 | A | | 11/1962 | Krause et al. | 343/874 |
| 3,760,812 | A | | 9/1973 | Timm et al. | 128/418 |
| 3,774,452 | A | | 11/1973 | Tullos et al. | 73/418 |
| 4,266,532 | A | | 5/1981 | Ryaby et al. | 128/1.5 |
| 4,439,702 | A | | 3/1984 | Belikov et al. | 310/80 |
| 4,489,276 | A | | 12/1984 | Yu | 324/338 |
| 4,832,051 | A | | 5/1989 | Jarvik et al. | 128/784 |
| 5,077,934 | A | | 1/1992 | Liboff et al. | 47/1.3 |
| 5,079,458 | A | | 1/1992 | Schuster | 310/12 |
| 5,173,669 | A | * | 12/1992 | Manoly | 333/162 |
| 5,359,340 | A | | 10/1994 | Yokota | 343/792 |
| 5,366,493 | A | | 11/1994 | Scheiner et al. | 607/116 |
| 5,464,456 | A | | 11/1995 | Kertz | 47/1.3 |
| 5,654,723 | A | | 8/1997 | Craven et al. | 343/742 |
| 5,819,467 | A | | 10/1998 | Zucker | 47/1.3 |
| 5,892,480 | A | | 4/1999 | Killen | 343/385 |
| 5,909,165 | A | | 6/1999 | Leopold | 335/210 |

(Continued)

FOREIGN PATENT DOCUMENTS

| GB | 479841 | * | 8/1935 |
| GB | 479841 | | 2/1938 |

(Continued)

*Primary Examiner* — Christine H Matthews
*Assistant Examiner* — Sunita Reddy
(74) *Attorney, Agent, or Firm* — Pillsbury Winthrop Shaw Pittman LLP

(57) ABSTRACT

An electrical system having an underlying structure resembling the double helix most commonly associated with DNA is used to produce useful electromagnetic fields for health applications and/or medical applications.

15 Claims, 4 Drawing Sheets

(56) References Cited

U.S. PATENT DOCUMENTS

| | | | |
|---|---|---|---|
| 5,954,630 A | 9/1999 | Masaki et al. | 600/28 |
| 6,005,462 A | 12/1999 | Myers | 335/220 |
| 6,169,523 B1 | 1/2001 | Ploussios | 343/895 |
| 6,239,760 B1 * | 5/2001 | Van Voorhies | 343/742 |
| 6,300,920 B1 | 10/2001 | Pertl et al. | 343/895 |
| 6,552,530 B1 | 4/2003 | Vaiser et al. | 324/204 |
| 6,770,023 B2 | 8/2004 | Vaiser et al. | 600/13 |
| 6,921,042 B1 | 7/2005 | Goodzeit et al. | 242/430 |
| 7,148,783 B2 | 12/2006 | Parsche et al. | 336/225 |
| 7,154,368 B2 | 12/2006 | Sweeney et al. | 336/229 |
| 7,375,449 B2 | 5/2008 | Butterfield | 310/207 |
| 8,463,407 B2 | 6/2013 | Bulkes et al. | 607/148 |
| 8,652,023 B2 | 2/2014 | Schmidt | 600/13 |
| 8,653,925 B2 | 2/2014 | Schmidt | 336/188 |
| 8,749,333 B2 | 6/2014 | Schmidt | 336/73 |
| 2005/0121396 A1 | 6/2005 | Kosakewich | 210/748 |
| 2008/0161884 A1 | 7/2008 | Chandler et al. | 607/50 |
| 2008/0266203 A1 | 10/2008 | Rossetto et al. | 345/895 |
| 2009/0206974 A1 | 8/2009 | Meinke | 336/224 |
| 2010/0005711 A1 | 1/2010 | McNeff | 47/1.4 |
| 2010/0057655 A1 | 3/2010 | Jacobson et al. | 706/45 |
| 2010/0179630 A1 | 7/2010 | Williams | 607/127 |
| 2012/0223800 A1 | 9/2012 | Schmidt | 336/229 |
| 2013/0192129 A1 | 8/2013 | Schmidt | 471/1.3 |
| 2013/0211181 A1 | 8/2013 | Schmidt | 600/13 |
| 2013/0285782 A1 | 10/2013 | Schmidt | 336/73 |
| 2014/0097925 A1 | 4/2014 | Schmidt | 336/188 |
| 2014/0218149 A1 | 8/2014 | Schmidt | 336/73 |

FOREIGN PATENT DOCUMENTS

| | | |
|---|---|---|
| GB | 2480610 | 11/2011 |
| WO | WO 2012/118971 | 9/2012 |
| WO | WO 2013/112810 | 8/2013 |
| WO | WO 2013/123009 | 8/2013 |

* cited by examiner

HEALTH APPLICATIONS OF A DOUBLE HELIX CONDUCTOR

RELATED APPLICATIONS

This application claims priority to U.S. Patent Application Ser. No. 61/633,593, entitled "Health Applications Of A Double Helix Conductor," and filed Feb. 13, 2012. This application is related to U.S. patent application Ser. No. 13/213,604, entitled "Double Helix Conductor," and filed Aug. 19, 2011, as well as U.S. patent application Ser. No. 13/457,347, entitled "System Configuration Using A Double Helix Conductor," and filed Apr. 26, 2012, as well as U.S. patent application Ser. No. 13/458,716, entitled "Health Applications of a Double Helix Conductor," and filed Apr. 27, 2012. These applications are hereby incorporated by reference into the present application in their entirety.

FIELD OF THE INVENTION

The invention relates to bodies structured as helically wound runners around which one or more conductive wires may be wound, electrical devices and/or systems configured to include such bodies, and the health/medical applications thereof.

BACKGROUND OF THE INVENTION

It is known that spirally wound electrical conductors exhibit certain electromagnetic properties and/or can be used to generate particular electromagnetic fields. For example, it is known that an electromagnetic coil may act as an inductor and/or part of a transformer, and has many established useful applications in electrical circuits. Applications of an electromagnetic coil may exploit the electromagnetic field that is created when, e.g., an active current source is operatively coupled to the coil.

SUMMARY

One aspect of the invention relates to a system for providing therapy to a subject and/or promoting health effects in a subject. The system includes a body, and one or more conductive wires. The body includes two intertwined helically wound runners arranged in at least two complete revolutions per runner. The body is arranged in a toroidal shape having a centroid. The centroid is arranged at or near one or both of a subject and/or a body part of the subject. The first wire is wound spirally around the first runner. The first wire is conductive. Two leads of the first wire are configured to be electrically coupled with a current source to receive a first current through the first wire along the first runner such that an electromagnetic field is created at or near the centroid that provides therapy to the subject.

One aspect of the invention relates to a system for providing therapy to a subject and/or promoting health effects in a subject. The system includes a body, a first wire, a second wire, two leads of the first wire, two leads of the second wire, and one or more resistive elements. The body includes two intertwined helically wound runners arranged in at least two complete revolutions per runner. The body is arranged in a toroidal shape having a centroid. The centroid is arranged at or near one or both of a subject and/or a body part of the subject. The first wire is carried by the first runner. The first wire is conductive. The first wire is spirally wound around the first runner to form a bifilar coil around the first runner. The second wire is carried by the second runner. The second wire is conductive. The second wire is spirally wound around the second runner to form a second bifilar coil around the second runner. The two leads of the first wire are configured to be electrically coupled to a current source to receive a first current through the first wire such that an electromagnetic field is created at or near the centroid. The electromagnetic field provides therapy to the subject. The two leads of the second wire are configured to be electrically coupled to the current source to receive a second current through the second wire such that the electromagnetic field is modified. The one or more resistive elements are electrically coupled to one or both of the first wire and/or the second wire such that a nominal impedance of the first wire, the second wire, and the one or more resistive elements has a predetermined value that substantially matches an impedance of the current source.

One aspect of the invention relates to a system for providing therapy to a subject and/or promoting health effects in a subject. The system includes a body, a first wire, one or more processors, a sound input module, and a playback module. The body includes two intertwined helically wound runners arranged in at least two complete revolutions per runner. The body is arranged in a toroidal shape having a centroid. The centroid is arranged at or near one or both of a subject and/or a body part of the subject. The first wire is carried by the first runner. The first wire is conductive. The first wire is spirally wound around the first runner. The first wire includes two leads configured to be electrically coupled to a current source to receive a first current through the first wire such that an electromagnetic field is created at or near the centroid of the toroidal shape of the body. The electromagnetic field provides therapy to the subject. The one or more processors are configured to execute computer program modules. The computer program modules include the sound input module and the playback module. The sound input module is configured to obtain sound information. The playback module is configured to produce sound signals based on the obtained sound information. The sound signals produced by the playback module are electrically coupled to the two leads of the first wire such that the first current corresponds to the sound signals.

One aspect of the invention relates to a method for providing therapy to a subject and/or promoting health effects in a subject. The method includes arranging a body at or near one or both of the subject and/or a body part of the subject. The body includes at least two intertwined helically wound runners arranged in at least two complete revolutions per runner. The body is arranged in a toroidal shape having a centroid. The body further includes a first wire carried by a first runner. The first wire is spirally wound around the first runner. The first wire is conductive. The first wire includes two leads configured to be electrically coupled to a current source to receive a first current through the first wire. The method further includes supplying the first current to the two leads of the first wire such that an electromagnetic field is created at or near the centroid. The electromagnetic field provides therapy to the subject.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
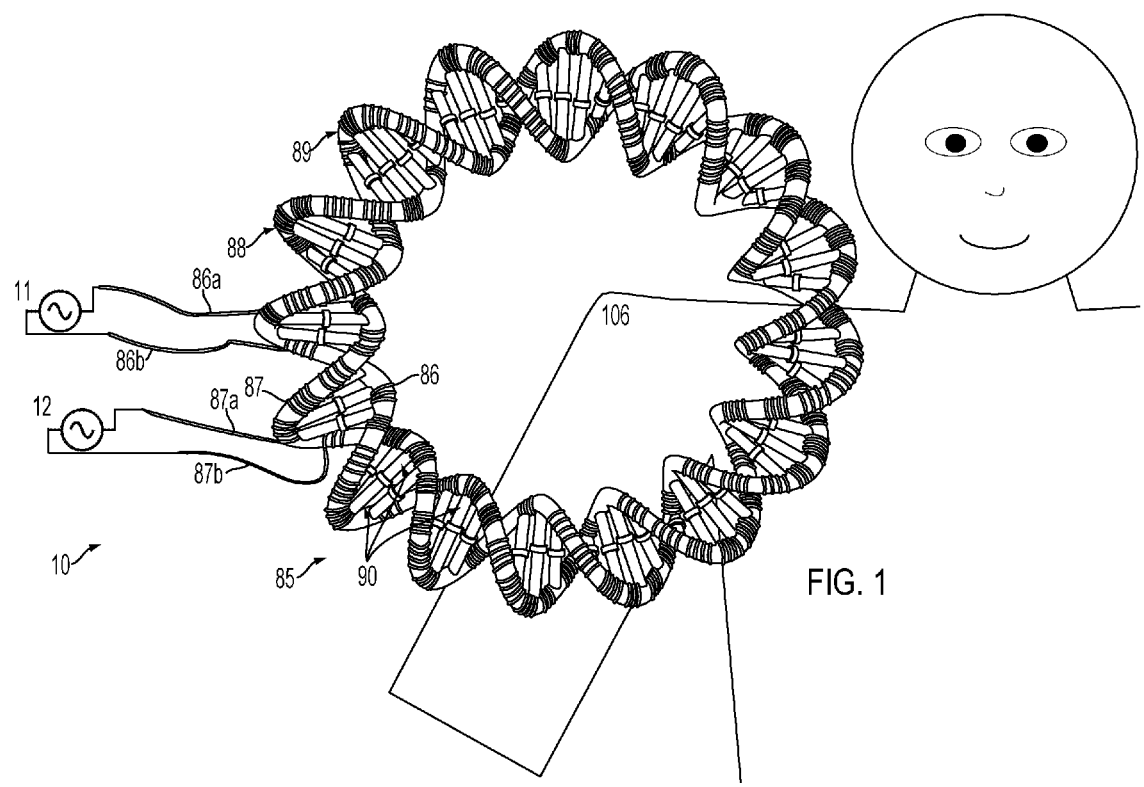
FIG. 1 schematically illustrates a system for providing therapy to a subject and/or promoting health effects in a subject, according to one or more embodiments.

FIG. 1 illustrates a system 10 for providing therapy to a subject 106 and/or promoting health effects in subject 106, according to one or more embodiments. The therapy and/or health effects may include, but are not limited to, one or more of pain relief, relief of discomfort, reduction of inflammation, improved range of motion, hair growth, tissue repair, regenerative effects, improved circulation, improved micro-circulation, and/or other types of therapy and/or health effects on living organisms. System 10 may include a body 85, a first wire 86, a current source 11, and/or other components. The depiction of the size of subject 106 relative to the size of body 85 is not meant to be limiting.

Body 85 of system 10 in FIG. 1 includes two intertwined helically wound runners—runner 88 and runner 89—sharing the same (circular) axis, coupled by struts 90 and having one or more conductive wires spirally wound around one or both runners. In other words, runner 88 and runner 89 of body 85 form cores around which wire 86 and wire 87 are spirally wound, respectively. As depicted in FIG. 1, body 85 includes two wires: wire 86 and wire 87. In some embodiments, system 10 includes one runner, three runners, and/or another number of runners.

Runner 88 and runner 89 of body 85 and system 10 in FIG. 1 are arranged in the shape of a three-dimensional curve similar to or substantially the same as a helix, bend with its ends arranged together. It is noted that the shape of body 85 resembles the general shape of DNA. The shape of the cross-section of a runner may include one or more of a circle, an oval, a square, a triangle, a rectangle, an angular shape, a polygon, and/or other shapes. The width and height of the cross-section of a runner may be limited for practical purposes. For example, for the purposes described herein, in some embodiments, it may be preferable to arrange body 85 such that there is available space within the periphery of body 85, as shown, e.g., in FIG. 1. As depicted in FIG. 1, the shape of the cross-section of runner 88 and runner 89 may be a circle. Note that embodiments of this disclosure are not intended to be limited by any of the given examples.

Runner 88, runner 89 and/or struts 90 of system 10 in FIG. 1 may be manufactured from one or more of plastic, plastic plated with metals including copper, nickel, iron, soft iron, nickel alloys, and/or other metals and alloys, and/or other materials. In some embodiments, runner 88, runner 89 and struts 90 are manufactured from non-conductive material. Runner 88, runner 89, and struts 90 may be manufactured from different materials. Runner 88, runner 89, and struts 90 may be manufactured through integral construction or formed separately prior to being assembled. The preceding statement is not intended to limit the (process of) manufacture of bodies similar to or substantially the same as body 85 in any way.

Referring to FIG. 1, wire 86 and wire 87, as any wire listed in any figure included in this description, may be insulated, uninsulated, or partially insulated and partially uninsulated.

The shape of body 85 of system 10 in FIG. 1 may be generally toroidal. In some embodiments, the body of system 10 may be arranged in any planar shape, including circular, polygonal, and/or other shapes. Alternatively, and/or simultaneously, a body such as body 85 may be arranged in a three-dimensional curve (a.k.a. space curve). Runner 88 and runner 89 of body 85 may form cores around which wire 86 and wire 87 are spirally wound, respectively. As such, wire 86 and wire 87 may be arranged in a helical shape having axes that coincide with runner 88 and runner 89, respectively. As shown in FIG. 1, wire 86 and 87 may be wound such that they go around any of struts 90 of body 85 and/or around any points of engagement between one of struts 90 and one of runners 88 and 89. The number of wire turns per complete revolution of a runner and/or the number of wire turns between adjacent struts may be characteristic measurements/features of body 85. In FIG. 1, wire 86 and wire 87 are arranged to make approximately three to five turns between adjacent struts associated with runner 88 and runner 89, respectively, and/or some other number of turns. The depiction of FIG. 1 is intended to be exemplary, and in no way limiting.

Wire 86 may include two leads—lead 86a and lead 86b. Wire 87 may include two leads—lead 87a and lead 87b. In system 10, body 85 is electrically coupled with one or more power sources and/or current sources, such as, e.g., current source 11 and/or a current source 12, arranged such that electrical coupling with one or both of wire 86 and wire 87 may be established, e.g. through coupling of current source 11 with lead 86a and 86b of wire 86 and through coupling of current source 12 with lead 87a and 87b of wire 87. The current supplied to wire 86 may be a direct current or an alternating current. The current supplied to wire 87 may be a direct current or an alternating current. The currents supplied to wire 86 and wire 87 may flow in the same direction or the opposite direction. In some embodiments, the leads of wire 86 and wire 87 may be electrically coupled with the same current source.

For alternating currents, operating frequencies ranging from 0 Hz to 100 GHz are contemplated. Operating currents ranging from 1 pA to 10 A are contemplated. Operating voltages ranging from 1 mV to 20 kV are contemplated. In some embodiments, a root mean square voltage of less than about 1.6 V is supplied to wire 86 and/or wire 87. In some embodiments, a root mean square voltage of greater than about 0.25 V is supplied to wire 86 and/or wire 87. In a preferred embodiment, the frequency of the alternating current supplied to wire 86 and/or wire 87 is between 0 Hz and 20 kHz. In some embodiments, the current is less than about 1 pA, 1 nA, 1 mA, 100 mA, 250 mA, 500 mA, and/or other amounts of current. The operating frequencies for wire 86 and wire 87 may be the same or different. Other electrical operating characteristics of current supplied to wire 86 and wire 87, such as phase, may be the same or different. System 10 may be used to exploit the electromagnetic field that is created in and/or around body 85 when electrical power is supplied to one or more wires of body 85. The electromagnetic field provides therapy to subject 106 and/or promotes health effects in a subject.

For the purposes of this description, the electromagnetic field may be an electromagnetic field of at least a predetermined threshold level of tesla. The predetermined threshold may be 1 pT, 1 nT, 1 mT, 10 mT, 100 mT, and/or another threshold.

Some embodiments of an electrical system including a body similar to or substantially the same as body 85 in FIG. 1, thus including wire 86 and wire 87, may be configured to have a current in wire 86 flowing in the opposite direction as the current in wire 87. In some embodiments the current supplied to one wire may be a direct current, whereas the current supplied to another wire may be an alternating current. By way of non-limiting example, additional structures for a body and/or electrical systems using a body may be described in U.S. patent application Ser. No. 13/457,347, filed Apr. 26, 2012, titled "System Configuration Using A Double Helix Conductor," and published as United States Patent Application Publication No. 2013/0211181, which is hereby incorporated into this disclosure by reference in its entirety. This patent application may also be referred to as "the '347 application" herein.

Some embodiments of an electrical system including a body similar to or substantially the same as body 85 may be configured to include one or more conductive wires that are wound to form a bifilar coil around one or more runners. In some embodiments, the windings may be one or more of caduceus windings, Ayrton-Perry winding, trifilar windings, windings of braided wires, and/or other types of windings. By way of non-limiting example, additional windings may be described in the '347 application.

In some embodiments, system 10 may include multiple bodies similar to or substantially the same as body 85. Currents for these multiple bodies may be supplied by one or more power sources and/or current sources.

In some embodiments, body 85 may be configured such that the dimensions of the available space within the periphery of body 85 and/or the passage formed through the centroid of the shape of body 85 are predetermined dimensions. In some embodiments, a predetermined dimension may include a diameter of about 1 inch, about 1 foot, about 2 feet, about 4 feet, about 6 feet, and/or another suitable dimension. Suitable dimensions may depend on average sizes of human fingers, wrists, elbows, arms, ankles, knees, legs, shoulders, (lower) backs, torsos, bodies, and/or other body parts, as may be used as an area to receive treatment and/or therapy.

In some embodiments, lead 86a and 86b of wire 86 and lead 87a and 87b of wire 87 are electrically coupled in the same circuit. This circuit may include, for example, one or more resistive components, such as resistors, that are arranged such that the circuit has a nominal impedance of a predetermined value, such as, e.g., 4 ohms, 8 ohms, 16 ohms, 32 ohms, 100 ohms, 600 ohms, and/or another predetermined value. In some embodiments, the predetermined value may be chosen to match the impedance of standard consumer electronics components and/or systems, including for example audio consumer electronics. These examples are not intended to be limiting in any way. By way of non-limiting example, additional information regarding resistive elements and/or impedance matching may be described in the '347 application.

Figure 2:
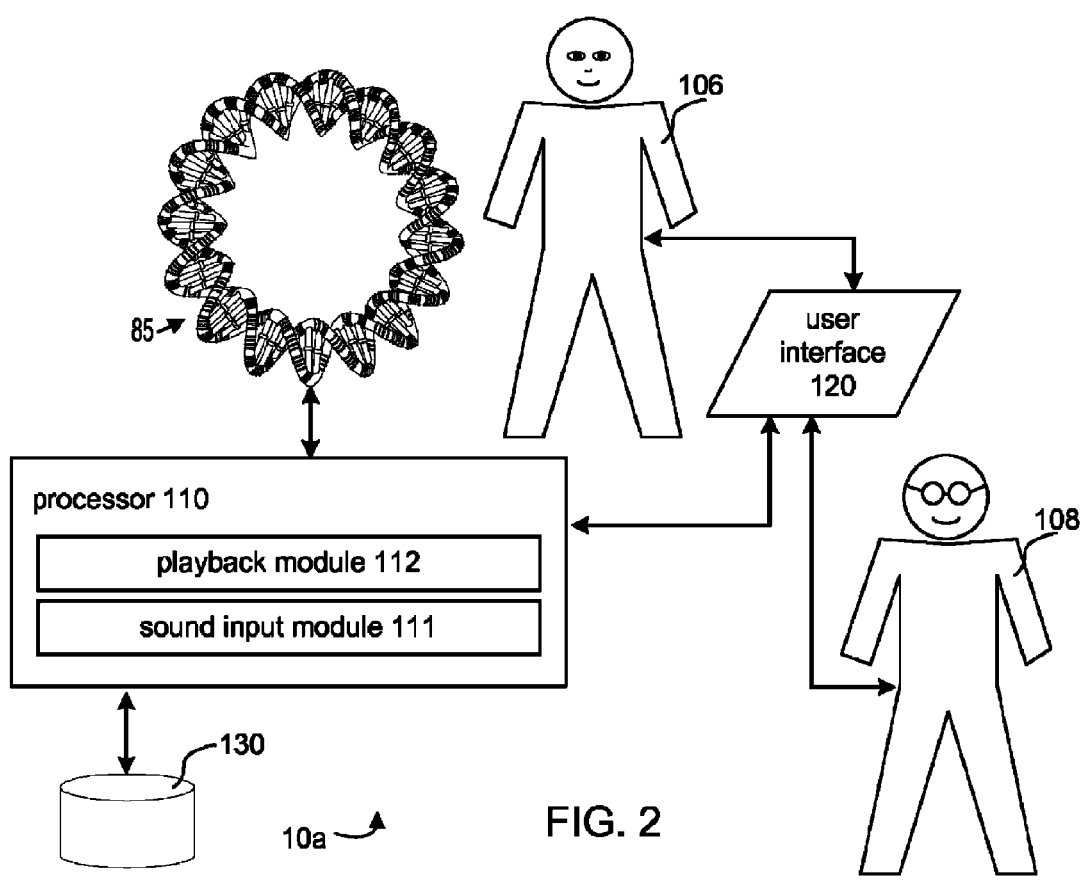
FIG. 2 schematically illustrates a system for providing therapy to a subject and/or promoting health effects in a subject, according to one or more embodiments.

By way of illustration, FIG. 2 schematically illustrates a system 10a for providing therapy to a subject and/or promoting health effects in a subject. System 10a may include one or more of body 85, processor 110, user interface 120, electronic storage 130, and/or other components. Body 85 in FIG. 2 may be similar to or substantially the same as body 85 in FIG. 1, described above. Specifically, body 85 in FIG. 2 may include any of the features, functions, and/or structures described herein in relation to body 85 of FIG. 1. Referring to FIG. 2, the one or more wires of body 85 are configured to receive current through the leads of the wires such that an electromagnetic field is created at or near the centroid of the toroidal shape of body 85. The electromagnetic field provides therapy to subject 106 and/or promotes health effects in subject 106.

Processor 110 of system 10a in FIG. 2 is configured to provide information processing capabilities in system 10a. As such, processor 110 includes one or more of a digital processor, an analog processor, a digital circuit designed to process information, a central processing unit, a graphics processing unit, an analog circuit designed to process information, a state machine, and/or other mechanisms for electronically processing information. Although processor 110 is shown in FIG. 2 as a single entity, this is for illustrative purposes only. In some embodiments, processor 110 may include a plurality of processing units.

As is shown in FIG. 2, processor 110 is configured to execute one or more computer program modules. The one or more computer program modules include one or more of a sound input module 111, a playback module 112, and/or other modules. Processor 110 may be configured to execute modules 111-112 by software; hardware; firmware; some combination of software, hardware, and/or firmware; and/or other mechanisms for configuring processing capabilities on processor 110.

It should be appreciated that although modules 111-112 are illustrated in FIG. 2 as being co-located within a single processing unit, in embodiments in which processor 110 includes multiple processing units, one or more of modules 111-112 may be located remotely from the other modules. The description of the functionality provided by the different modules 111-112 described herein is for illustrative purposes, and is not intended to be limiting, as any of modules 111-112 may provide more or less functionality than is described. For example, one or more of modules 111-112 may be eliminated, and some or all of its functionality may be incorporated, shared, integrated into, and/or otherwise provided by other ones of modules 111-112. Note that processor 110 may be configured to execute one or more additional modules that may perform some or all of the functionality attributed below to one of modules 111-112.

Sound input module 111 may be configured to obtain sound information. In some embodiments, the sound information may be obtained through a microphone or other acoustic-to-electric transducer and/or sensor. In some embodiments, the sound information may be obtained from storage, e.g. from electronic storage. Sound information obtained from storage may include electronic audio files in any format, including but not limited to MP3, WMA, WAV, AIFF, and/or other audio formats. Audio formats may be uncompressed, have lossless compression, and/or lossy compression. Sound information may be obtained from traditional sound sources including phonographs, CD-players, DVD players, AM radio, FM radio, and/or other sound sources. Electronic storage may be local to system 10a and/or be accessible from a remote location through a network connection, such as e.g. the internet.

Playback module 112 may be configured to produce sound signals based on the obtained sound information. The sound signals produced by playback module 112 may be analog and/or digital signals. The sound signals produced by playback module 112 may be electric, optical, and/or using other media. The sound signals produced by playback module 112 may be accessible through one or more signal connectors, including but not limiting to line out connectors, tip-ringsleeve (TRS) connectors, tip-ring-ring-sleeve (TRRS) connectors, TOSLINK connectors, S/PDIF connectors, FireWire™ connectors, HDMI connectors, DVI connectors, USB connectors, and/or other connectors capable of transferring an audio signal. The sound signals produced by playback module 112 may be electrically coupled to the leads of the one or more conductive wires of body 85 (depicted in FIG. 2) such that current through the one or more conductive wires of body 85 corresponds to the produced sound signals.

In some embodiments, the sound signals produced by playback module 112 may be amplified by an amplifier before being electrically coupled to the leads of the one or more conductive wires of body 85. In some preferred embodiments, the amplifier may be an audio amplifier ranging between 100 W and 400 W. Other types of amplifiers and/or amplifiers having a different power range are also contemplated.

In some embodiments, the sound information obtained by sound input module 111 may include and/or correspond to sounds that are traditionally used in sound therapy and/or sound healing. For example, sound signals having one or more specific frequencies, waveforms, wave shapes, and/or amplitudes may have regenerative effects and/or other health effects. In some embodiments, the sounds may include human voices producing one or more of the following sounds: "Om," "Uh," "Ooo,", "Oh," "Ah," "Eye," "Aye," "Eee," and/or other sounds and/or phrases. In some embodiments, playback module 112 may be configured to loop and/or repeat particular sound information, e.g. a particular track on a CD or a particular MP3 file, for a predetermined amount of time, indefinitely, and/or as instructed by subject 106 and/or user 108.

Electronic storage 130 of system 10a in FIG. 2 comprises electronic storage media that electronically stores information. The electronic storage media of electronic storage 130 may include one or both of system storage that is provided integrally (i.e., substantially non-removable) with system 10a and/or removable storage that is removably connectable to system 10a via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10a to function properly. For example, electronic storage 130 may store sound information and/or electronic audio files (as discussed elsewhere herein), and/or other information. Electronic storage 130 may be a separate component within system 10a, or electronic storage 130 may be provided integrally with one or more other components of system 10a (e.g., processor 110).

User interface 120 of system 10a in FIG. 2 is configured to provide an interface between system 10a and a user (e.g., user 108, subject 106, a caregiver, a therapy decision-maker, etc.) through which the user can provide information to and receive information from system 10a. This enables data, results, and/or instructions and any other communicable items, collectively referred to as "information," to be communicated between the user and system 10a. An example of information that may be conveyed to user 108 is an indication of the volume and/or intensity of the sound signals produced by playback module 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10a from removable storage (e.g., a smart card, a flash drive, a removable disk, etc.) that enables the user(s) to customize system 10a. Other exemplary input devices and techniques adapted for use with system 10a as user interface 120 include, but are not limited to, an RS-232 port, RF link, an IR link, modem (telephone, cable, Ethernet, internet or other). In short, any technique for communicating information with system 10a is contemplated as user interface 120.

Figure 4:
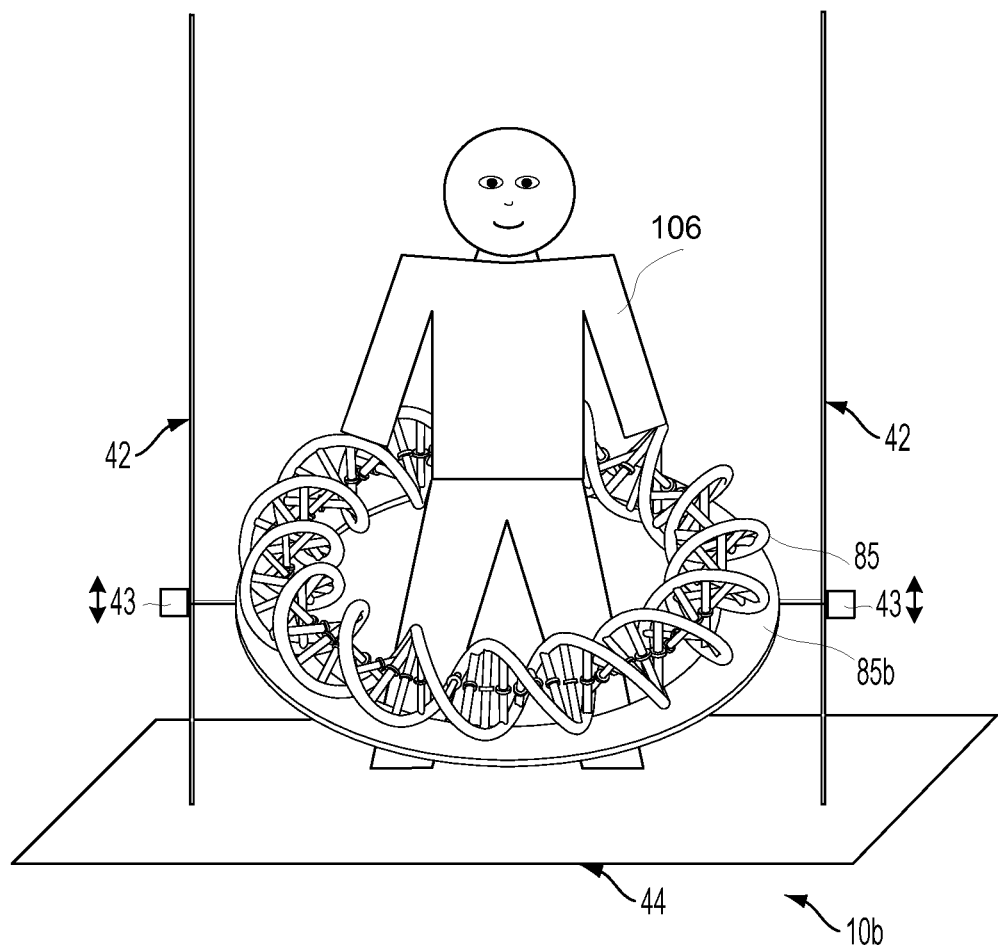
FIG. 4 schematically illustrates a system for providing therapy to a subject and/or promoting health effects in a subject, according to one or more embodiments.

FIG. 4 schematically illustrates a system 10b for providing therapy to subject 106 and/or promoting health effects in subject 106. System 10b may include one or more of body 85, support structure 85b, one or more supporting posts 42, support structure 44, one or more raising mechanisms 43, and/or other components. Body 85 in FIG. 4 may be similar to or substantially the same as body 85 in FIG. 1 or FIG. 2, described above. Specifically, body 85 in FIG. 4 may include any of the features, functions, and/or structures described herein in relation to body 85 of FIG. 1 or FIG. 2. Referring to FIG. 4, the one or more wires of body 85 are configured to receive current through the leads of the wires such that an electromagnetic field is created at or near the centroid of the toroidal shape of body 85. The electromagnetic field provides therapy to subject 106 and/or promotes health effects in subject 106.

Support structure 44 may be configured to support one or more of subject 106, supporting posts 42, body 85, and/or other components of system 10b. In some embodiments, support structure 44 may include a platform and/or base.

Support structure 85b may be configured to support body 85. Support structure 85b may be configured to mechanically couple to one or more of support posts 42, raising mechanism 43, and/or support structure 44. In some embodiments, support structure 85b may include a shelf and/or tray. Support structure 85b may include an open area in the center that coincides with a passage formed through body 85 such that support structure 85b and body 85 may be moved relative to the position of subject 106 within and/or inside that passage. In other words, body 85 may be disposed around subject 106 and/or move up and down to cover different body parts of subject 106. For example, the movement of support structure 85b and body 85 may be substantially vertical, as depicted in FIG. 4. Note that this example is not intended to be limiting. Embodiments in which subject 106 is placed in a substantially horizontal position are also contemplated. In such a case, the position of other components, which may include body 85, support structure 85b, supporting posts 42, and/or other components, may be adjusted accordingly.

Supporting posts 42 may be configured to support one or more of body 85, support structure 85b, raising mechanism 43, and/or other components of system 10b. The depiction of two supporting posts 42 in FIG. 4 is not intended to be limiting.

Raising mechanism 43 may be configured to move body 85 and/or support structure 85b in a predetermined manner or path. For example, the predetermined path may be up and down, as depicted in FIG. 4 and indicated by the arrows near raising mechanism 43. The depiction of two raising mechanisms 43 in FIG. 4 is not intended to be limiting. In some embodiments, raising mechanism 43 may include an electric motor and/or lift.

Control of one or more raising mechanisms 43 during operation of system 10b may include one or more of a determination of a starting position relative to subject 106 and/or supporting structure 44, a determination of a direction for the movement of body 85 and/or support structure 85b relative to the orientation and position of system 10b, a determination of the speed of the movement, a determination of the range of movement (e.g. in relation to a particular body part of subject 106), a determination of the number of sweeps across (all or part of) subject 106, a determination of the intensity level, frequency, and/or particular sound information corresponding to the electromagnetic field used, which may vary depending on the position of body 85 or along different parts of subject 106, and/or other operating conditions of system 10b. For example, to treat a specific back problem for a particular subject, raising mechanism 43 may be controlled to start at the center of the intended area of treatment, and may be subsequently controlled to sweep across a predetermined range of movement, e.g. a range of 10 inches on either side of the center, for a predetermined period or a predetermined number of sweeps, as intended for body 85 and/or support structure 85b to provide treatment as prescribed. In some embodiments, control of the operating conditions of system 10b may be implemented by a computer program module that is executed by a processor. For example, a set of sweeps as described above in relation to a specific back problem may be controlled programmatically by a computer program module.

Figure 3:
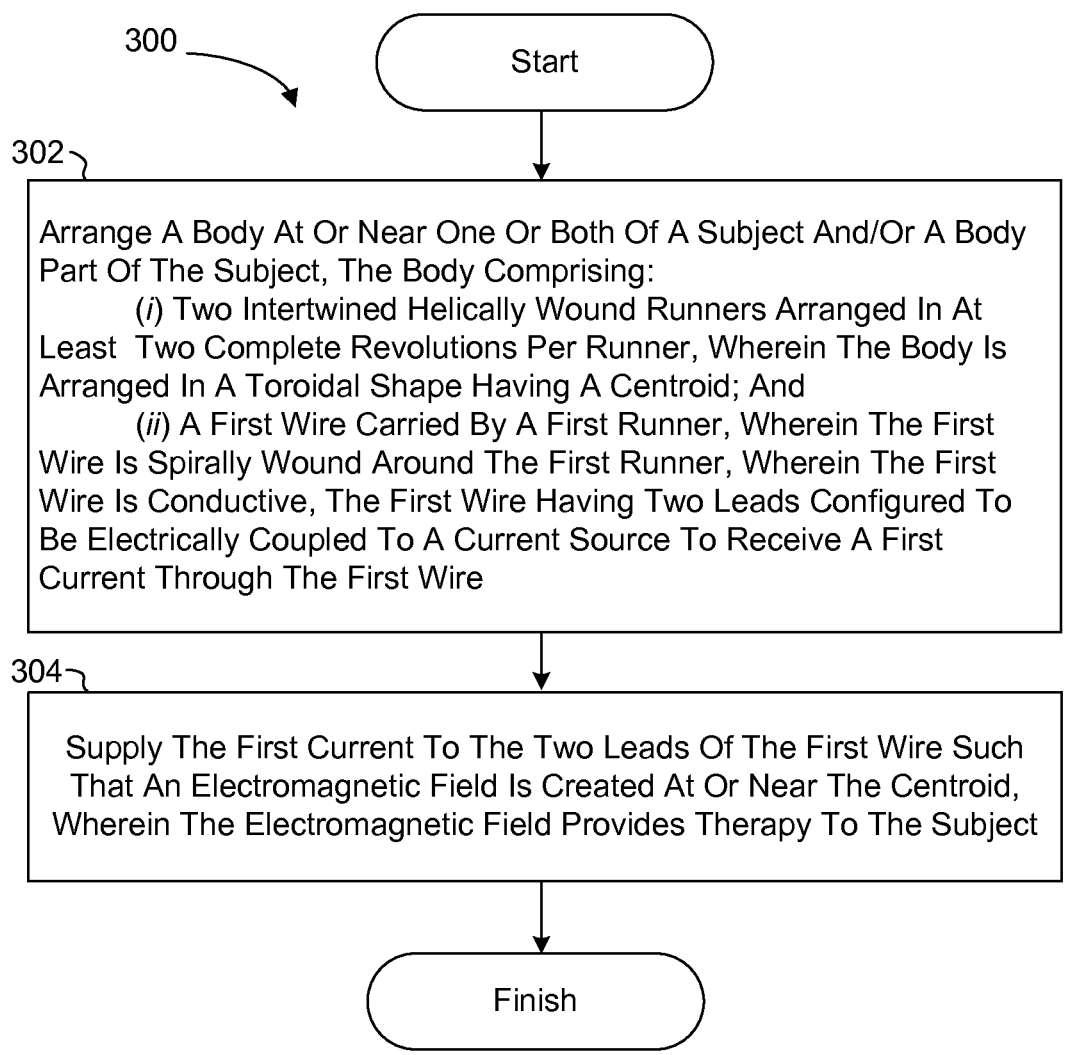
FIG. 3 illustrates a method for providing therapy to a subject and/or promoting health effects in a subject, according to one or more embodiments.

FIG. 3 illustrates a method 300 for providing therapy to a subject. The operations of method 300 presented below are intended to be illustrative. In certain embodiments, method 300 may be accomplished with one or more additional operations not described, and/or without one or more of the operations discussed. Additionally, the order in which the operations of method 300 are illustrated in FIG. 3 and described below is not intended to be limiting.

In certain embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a body is arranged at or near one or both of a subject and/or a body part of the subject. The body includes two intertwined helically wound runners, and a conductive wire. The runners are arranged in at least two complete revolutions per runner. The body is arranged in a toroidal shape having a centroid. The wire is carried by the first runner. The wire is spirally wound around the first runner. The wire has two leads configured to be electrically coupled to a current source to receive a first current through the wire. In one embodiment, operation 302 is performed by a user of system 10 (shown in FIG. 2 and described above).

At an operation 304, a current is supplied to the two leads of the wire such that an electromagnetic field is created at or near the centroid that provides therapy to the subject. In one embodiment, operation 304 is performed by a current source similar to or substantially the same as current source 11 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for providing therapy to a subject, the system comprising:
    a body including a first runner and a second runner, wherein the first runner is arranged in a first helical shape, wherein the body is arranged in a toroidal shape having a centroid, wherein the centroid is configured to be arranged at or near at least one of the subject and a body part of the subject;
    a first wire wound around the first runner of the body such that the first wire is arranged in a second helical shape formed around the first helical shape of the runner, wherein the first wire is conductive;
    a second wire wound around the second runner, wherein the second wire is conductive;
    two leads of the first wire configured to be electrically coupled with one or more current sources to receive a first current through the first wire along the first runner; and
    two leads of the second wire configured to be electrically coupled with the one or more current sources to receive a second current through the second wire along the second runner,
    wherein the second runner is arranged in a third helical shape that is intertwined with the first helical shape, wherein the first runner and second runner are arranged in a shape of a double helix, wherein the second wire is arranged in a fourth helical shape formed around the third helical shape of the second runner, wherein the first helical shape, the second helical shape, the third helical shape, and the fourth helical shape have the same handedness,
    wherein the first current and the second current create an electromagnetic field at or near the centroid that provides therapy to the subject.

2. The system of claim 1, wherein the first helical shape of the first runner is arranged within the second helical shape of the first wire.

3. The system of claim 1, wherein the first helical shape and the second helical shape both have right-handedness.

4. The system of claim 1, wherein the first helical shape has a first axis, wherein the second helical shape has a second axis, and wherein the second axis coincides with the first runner.

5. The system of claim 1, wherein the first runner is arranged in between 2 and 10000 revolutions in the body.

6. The system of claim 1, wherein the first wire is arranged in between 2 and 10000 revolutions per revolution of the first helical shape of the first runner.

7. The system of claim 1, wherein the first wire is wound such that the first wire forms a bifilar coil around the first runner.

8. The system of claim 1, wherein the first wire is wound such that the first wire forms a caduceus winding around the first runner.

9. The system of claim 1, further comprising the one or more current sources, wherein the one or more current sources are configured such that the first current through the first wire is an alternating current, wherein the alternating current has a frequency above 0 Hz and below 40 GHz.

10. The system of claim 9, wherein the one or more current sources are configured such that a root mean square voltage of less than about 1.6 V is supplied to the two leads of the first wire.

11. The system of claim 9, wherein the one or more current sources are configured such that a root mean square voltage of greater than about 0.25 V is supplied to the two leads of the first wire.

12. The system of claim 1, wherein the first helical shape, the second helical shape, the third helical shape, and the fourth helical shape have right-handedness.

13. The system of claim 1, wherein the third helical shape of the second runner is arranged within the fourth helical shape of the second wire.

14. The system of claim 1, wherein the body forms a passage through the centroid, and wherein the body is formed such that the passage through the centroid of the toroidal shape of the body has a diameter between about 1 inch and about 4 feet.

15. A system for providing therapy to a subject, the system comprising:
one or more physical processors configured to execute computer program modules, wherein the computer program modules include:
a sound input module that obtains sound information, wherein the sound information includes at least one or more sound therapy signals, and wherein the sound therapy signals have specific frequencies, waveforms, and/or wave shapes, and
a playback module that produces one or more sound signals based on the obtained sound information;

a body including a first runner and a second runner, wherein the first runner and second runner are helically intertwined, wherein the first runner is arranged in a first helical shape, wherein the second runner is arranged in a second helical shape, wherein the body is arranged in a toroidal shape having a centroid, wherein the centroid is configured to be arranged at or near at least one of the subject and a body part of the subject, and wherein the first runner and the second runner are arranged in a shape of a double helix;

a first wire wound around the first runner of the body such that the first wire is arranged in a third helical shape formed around the first helical shape of the first runner, wherein the first wire is conductive;

a second wire wound around the second runner of the body such that the second wire is arranged in a fourth helical shape formed around the second helical shape of the second runner, wherein the second wire is conductive;

one or more current sources, wherein the one or more current sources are configured to supply alternating current having a frequency above 0 Hz and below 40 GHz;

two primary leads of the first wire configured to be electrically coupled with the one or more current sources to receive a first alternating current through the first wire along the first runner, wherein the first alternating current creates an electromagnetic field at or near the centroid that provides therapy to the subject; and two secondary leads of the second wire configured to be electrically coupled with the one or more current sources to receive a second alternating current through the second wire along the second runner, wherein the second alternating current modifies the electromagnetic field, wherein the one or more current sources configured to supply the first alternating current and the second alternating current such that the first alternating current and the second alternating current correspond to the one or more produced sound signals.

* * * * *